United States Patent [19]

Ison

[11] Patent Number: Plant 5,822

[45] Date of Patent: Dec. 9, 1986

[54] GRAPEVINE NAMED ISON

[76] Inventor: Bill Ison, Rte. 1, Brooks, Ga. 30205

[21] Appl. No.: 670,051

[22] Filed: Nov. 9, 1984

[51] Int. Cl.[4] ..... A01H 5/03

[52] U.S. Cl. ..... Plt./47

[58] Field of Search ..... Plt./47

*Primary Examiner*—Robert E. Bagwill

*Attorney, Agent, or Firm*—Eugene T. Holmes

[57] ABSTRACT

A cross between the female variety Sugargate and the pollen parent variety Senoia, to produce an improved variety of self-fertile muscadine grape.

1 Drawing Figure

DESCRIPTION OF THE VARIETY

A cross between the female variety Sugargate and the pollen parent variety Senoia.

The primary objective of the breeding was to produce an improved variety of muscadine grape. The fruit of the new variety is large and bronze and has a dry stem scar. Other fruit characteristics of the new variety include even ripening, high sugar content and long shelf life. The new variety is self-fertile, as well as productive and vigorous.

In comparison with both the seed and the pollen parent, the new variety is similar in size to the seed parent and resembles in color the seed parent. The new variety is larger than the pollen parent. The fruit of this new variety contains on the average of from 20 to 21 percent soluble solids, which sugar content is higher than the pollen parent. The present variety yields approximately 4 to 6 tons per acre in tests conducted at Ison's Nursery & Vineyards, Brooks, Ga. The taste of this fruit is outstanding, having an excellent flavor.

Asexual reproduction of the new variety either by soft wood cuttings or by layering as performed at Brooks, Ga. shows that the foregoing characteristics and distinctions come true to form and are established and transmitted through succeeding propagations.

The accompanying photograph shows a typical specimen of the vegetative growth and fruit of the new variety when the fruit is ripe and ready for picking and as depicted in color as nearly true as it is reasonably possible to make the same in color illustration of the characteristics.

The following is a detailed description of the new variety:

Species: *Vitis rotundifolia.*
Type: Vine.
Seed parent: Variety Sugargate.
Pollen parent: Variety Senoia.
Propagation: Holds its characteristics through succeeding propagation by either layering or by soft wood cuttings.

Locality where grown: Brooks, Ga.
Fruit borne: Usually in clusters of 6 to 15 berries.
Fruit size: Large, similar in size as the seed parent, about $1\frac{1}{8}''$ diameter.
Fruit color: Greyed Purple Group 187A Fan 4 of The Royal Horticultural Society, London, England.
Sugar content: 20 to 21 percent soluble solids.
Fruit shape: Round.
Seed:
*Average diameter.*—$\frac{1}{8}$ inch.
*Average seed per berry.*—2.65.
Maturity date: Normally ripens about September 17, at Brooks, Ga.
Pulp:
A. *Color group.*—Fan 195A Fan 4 The Royal Horticultural Society, London, England.
B. *Consistency.*—Medium soft medium, juicy as compared to most muscadine varieties.
Skin: Thick.
Foliage:
*Leaf color.*—Fan 3 137A, The Royal Horticultural Society London, England.
*Leaf size and shape.*—Similar to most muscadine varieties.
Reproductive organs: Self-fertile.
Flowers: Perfect.
Growth habits: Vine requires support, vigorous and productive.
Canes: Medium to large calipers.
Diseases: Tolerant to Black Rot, Ripe Rot and other diseases specific to the muscadine.

This description was made from a muscadine vine grown at Ison's Nursery & Vineyards, Brooks, Ga.

DESCRIPTION OF THE DRAWING

There is attached hereto a permanently mounted color photograph accurately depicting the new plant and particularly the fruit and foliage thereof.

I claim:

1. The new and distinct variety of the specified plant as described and illustrated.

* * * * *

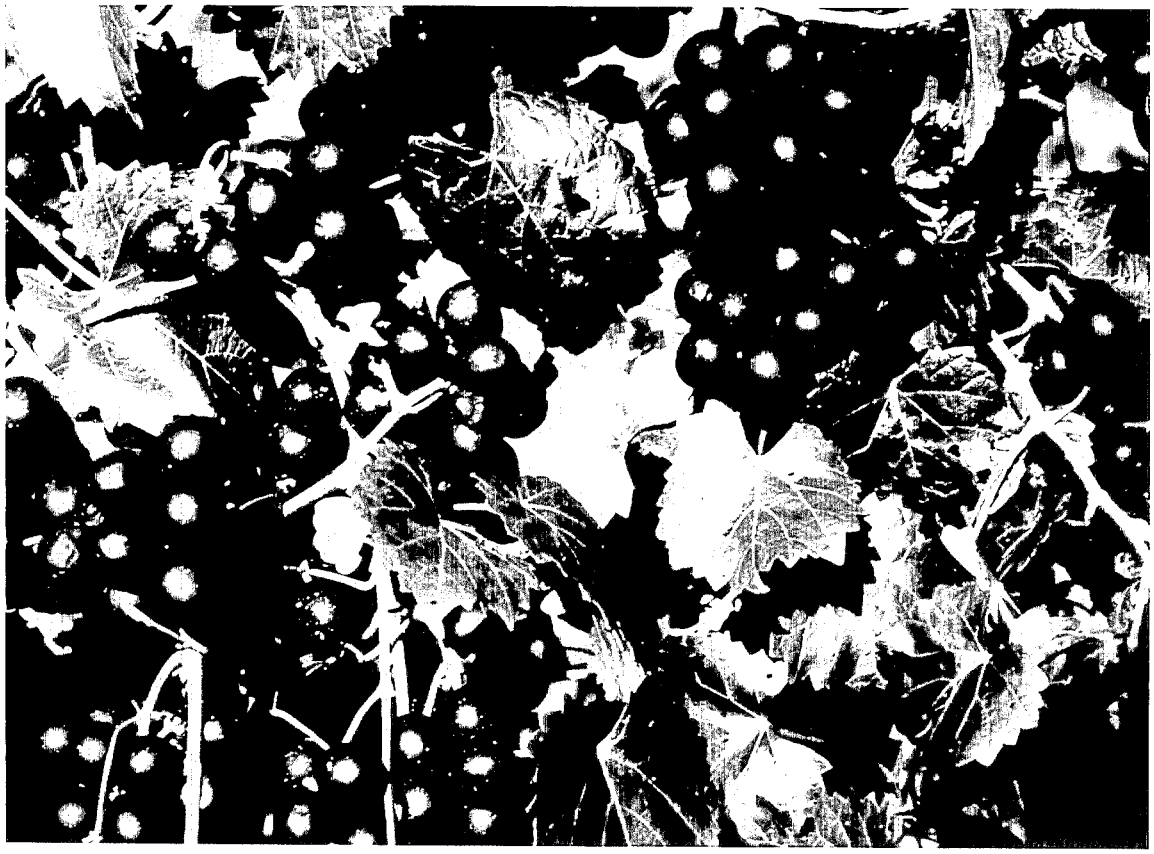

VARIETY "ISON"